United States Patent [19]

Slongo et al.

[11] Patent Number: 5,051,459

[45] Date of Patent: Sep. 24, 1991

[54] N-TRIAZINYLOXALAMIDES

[75] Inventors: Mario Slongo, Tafers; Jean-Luc Birbaum, Fribourg, both of Switzerland; Andreas Valet, Eimeldingen, Fed. Rep. of Germany

[73] Assignee: Ciba-Geigy Corporation, Ardsley, N.Y.

[21] Appl. No.: 490,816

[22] Filed: Mar. 8, 1990

[30] Foreign Application Priority Data

Mar. 17, 1989 [CH] Switzerland .................. 996/89

[51] Int. Cl.$^5$ .......................................... C08K 5/3492
[52] U.S. Cl. ........................................ 524/100; 252/403; 549/198; 549/207; 549/217; 549/219
[58] Field of Search ............... 524/100; 252/403; 544/198, 207, 217, 219

[56] References Cited

U.S. PATENT DOCUMENTS 4,003,875  1/1977  Lüthi et al. .................. 106/178

Primary Examiner—Kriellion S. Morgan
Attorney, Agent, or Firm—Luther A. R. Hall

[57] ABSTRACT

N-Triazinyloxalamides of formula I

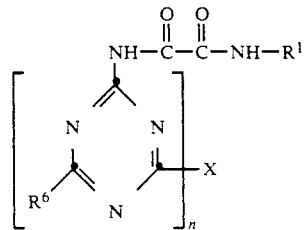

wherein n is 1-4 and $R^1$, $R^6$ and X are as defined in claim 1, are UV absorbers and are suitable as light stabilizers for organic materials.

10 Claims, No Drawings

N-TRIAZINYLOXALAMIDES

The invention relates to novel N-triazinyloxalamides and the use thereof as light stabilizers of the UV absorber type, and to the materials stabilized by means of these compounds.

Oxalic acid dianilides have been known for a long time as UV absorbers and are used as light stabilizers for organic materials which are damaged by UV light. Unsymmetrical oxalic acid dianilides with different aryl groups, for example those described in U.S. Pat. No. 4 003 875, are used in particular for this purpose.

Oxalic acid diamides substituted on one N atom by an aryl radical and on the other N atom by a triazinyl radical, or substituted on both N atoms by a triazinyl radical, were previously unknown. It has been found that such compounds can be prepared and that they absorb strongly in the UV region of 270-370 nm.

The invention relates to compounds of formula I

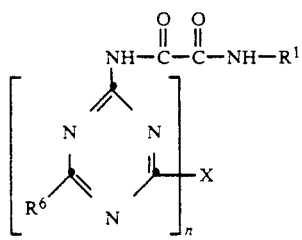

wherein n is an integer from 1 to 4, $R^1$ is a group of formula II or III

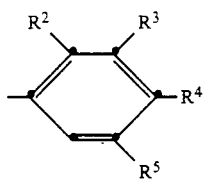

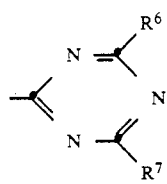

$C_5$-$C_{12}$ cycloalkyl, $C_7$-$C_9$ phenylalkyl, hydroxyl, $C_1$-$C_{12}$ alkoxy, phenoxy, phenoxy substituted by $C_1$-$C_4$ alkyl, $C_1$-$C_4$ alkoxy, halogen or hydroxyl, $C_2$-$C_{18}$ alkoxycarbonyl, $C_2$-$C_{18}$ alkylaminocarbonyl, a group —CO—O—$R^{10}$, $C_3$-$C_5$ alkenyl, $C_3$-$C_5$ alkynyl, $C_2$-$C_{12}$ alkanoyl, benzoyl, $C_1$-$C_8$ perfluoroalkyl chlorine, fluorine or bromine, with the proviso that the group of formula II contains no more than three hydroxyl groups, $R^6$ and $R^7$ independently of the other are $C_1$-$C_{12}$ alkoxy, $C_3$-$C_{12}$ cycloalkoxy, phenoxy, phenoxy substituted by $C_1$-$C_{12}$ alkyl, $C_3$-$C_5$ alkenyloxy, phenyl, pyridyl, phenyl substituted by hydroxyl, $C_1$-$C_{12}$ alkyl, $C_1$-$C_{12}$ alkoxy, $C_1$-$C_{12}$ alkylthio or $C_1$-$C_{12}$ monoalkylamino or dialkylamino, or a group —N($R^8$)($R^9$), wherein $R^8$ and $R^9$ independently of the other are hydrogen, $C_1$-$C_{18}$ alkyl, $C_3$-$C_{18}$ alkyl interrupted by one or more —O—, $C_3$-$C_5$ alkenyl, $C_2$-$C_4$ hydroxyalkyl or a group of formula IV

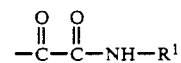

wherein $R^{11}$ is hydrogen, $C_1$-$C_4$ alkyl, $C_3$-$C_5$ alkenyl, $C_7$-$C_9$ phenylalkyl, $C_2$-$C_{12}$ alkanoyl, hydroxyl, $C_1$-$C_{12}$ alkoxy, $C_5$-$C_{12}$ cycloalkoxy or $C_2$-$C_{18}$ alkanoyloxy, or $R^8$ and $R^9$ together are $C_4$-$C_9$ alkylene which can be interrupted by —O—, and in the case where $R^8$ is hydrogen, $R^9$ can also be a group

$R^{10}$ is a group of formula IV and X in the case where n=1 is as defined for $R^6$, in the case where n=2 is a group —N($R^8$)—$R^{12}$—N($R^8$)—,

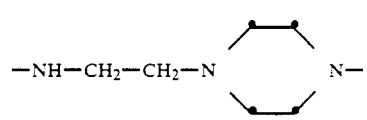

wherein $R^{12}$ is $C_2$-$C_{12}$ alkylene or $C_4$-$C_{12}$ alkylene interrupted by one or more —O—, in the case where n=3 is a group

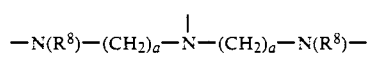

in the case where n=4 is a group

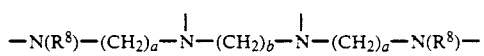

wherein a and b are 2 or 3.

If the substituent $R^2$, $R^3$, $R^4$, $R^5$, $R^8$ or $R^9$ in said compounds is $C_1$-$C_{18}$ alkyl, this can be an unbranched or branched alkyl group, e.g. methyl, ethyl, propyl, isopropyl, n-butyl, sec-butyl, tert-butyl, n-pentyl, n-hexyl, n-heptyl, n-octyl, 2-ethylhexyl, isononyl, n-decyl, sec-undecyl, n-dodecyl, n-tetradecyl, 1,1,3,3-tetramethylbutyl or n-octadecyl.

If $R^8$ or $R^9$ is $C_3$-$C_{18}$ alkyl interrupted by —O—, this can be e.g. 2-methoxyethyl, 2-butoxyethyl, 3-ethoxypropyl, 3,6-dioxaheptyl, 3,6-dioxaoctyl, 3,6,9-trioxadecyl or 3,6,9-trioxadodecyl.

$R^8$ or $R^9$ as $C_2$-$C_4$ hydroxyalkyl can be e.g. 2-hydroxyethyl, 2-hydroxypropyl, 2-hydroxybutyl or 3-hydroxypropyl. $R^2$, $R^3$, $R^4$ or $R^5$ as $C_1$-$C_8$ trifluoromethyl.

$R^2$, $R^3$, $R^4$ and $R^5$ as $C_5$-$C_{12}$ cycloalkyl can be e.g. cyclopentyl, cyclohexyl, cyclooctyl or cyclododecyl, especially cyclohexyl. $R^2$, $R^3$, $R^4$ or $R^5$ as $C_3$-$C_5$ phenylalkyl is especially benzyl.

$R^2$, $R^3$, $R^4$, $R^5$, $R^8$, $R^9$ or $R^{10}$ as $C_3$-$C_5$ alkenyl can be e.g. allyl, methallyl, but-2-enyl or 2,3-dimethylallyl, especially allyl. $R^2$, $R^3$, $R^4$ or $R^5$ as $C_3$-$C_5$ alkynyl is especially propargyl.

If $R^8$ and $R^9$ together are $C_4$-$C_9$ alkylene which can be interrupted by —O—, the group —N($R^8$)($R^9$) forms a heterocyclic ring, e.g. a pyrrolidine, piperidine, 2,2,6,6-tetramethylpiperidine or morpholine ring.

$R^{12}$ as $C_2$-$C_{12}$ alkylene or alkylene interrupted by —O— can be e.g. dimethylene to dodecylmethylene, 2,2-dimethyltrimethylene, 2,2,4-trimethylhexamethylene, 3-oxapentamethylene or 4-oxaheptamethylene. $R^{12}$ is preferably $C_2$-$C_8$ alkylene and especially hexamethylene. $R^2$, $R^3$, $R^4$, $R^5$, $R^6$, $R^7$ or $R^{11}$ as $C_1$-$C_{12}$ alkoxy can be e.g. methoxy, ethoxy, isopropoxy, n-butoxy, isopentoxy, n-hexyloxy, n-octyloxy, n-decyloxy or n-dodecyloxy. $R^6$ or $R^7$ as $C_3$-$C_{12}$ cycloalkoxy can be e.g. cyclopropoxy, cyclopentoxy, cyclohexyloxy, cyclooctyloxy or cyclododecyloxy, especially cyclohexyloxy. $R^{11}$ as cycloalkoxy is preferably cyclohexyloxy.

$R^2$, $R^3$, $R^4$, $R^5$ or $R^{11}$ as $C_2$-$C_{12}$ alkanoyl can be e.g. acetyl, propionyl, butyryl, isobutyryl, hexanoyl, octanoyl, decanoyl or dodecanoyl. $R^2$, $R^3$, $R^4$ or $R^5$ as $C_2$-$C_{18}$ alkoxycarbonyl or alkylaminocarbonyl can be e.g. methoxycarbonyl, ethoxycarbonyl, butoxycarbonyl, hexyloxycarbonyl, octyloxycarbonyl, dodecyloxycarbonyl, methylaminocarbonyl, dimethylaminocarbonyl, butylaminocarbonyl, octylaminocarbonyl or dodecylaminocarbonyl.

$R_{11}$ as alkanoyloxy can be e.g. acetoxy, propionoxy, butyroxy, hexanoyloxy, octanoyloxy or dodecanoyloxy. $R^6$ or $R^7$ as $C_3$-$C_5$ alkenyloxy can be e.g. allyloxy, methallyloxy or 2,5-dimethylallyloxy.

$R^1$ is preferably a group of formula II and n is preferably 1. Preferred compounds of formula I are those in which n is 1 or 2, $R^1$ is a group of formula II or III, $R^2$, $R^3$, $R^4$ and $R^5$ independently of the others are H, $C_1$-$C_{12}$ alkyl, cyclohexyl, benzyl, hydroxyl, $C_1$-$C_{12}$ alkoxy, phenoxy, phenoxy substituted by $C_1$-$C_4$ alkyl, $C_1$-$C_4$ alkoxy or Cl, $C_2$-$C_5$ alkoxycarbonyl, allyl, propargyl, $C_2$-$C_5$ alkanoyl, benzoyl, $CF_3$, Cl, F or Br, $R^6$ and $R^7$ independently of the other are $C_1$-$C_{12}$ alkoxy, cyclohexyloxy, phenoxy, tolyloxy, allyloxy or a group —N($R^8$)($R^9$), $R^8$ and $R^9$ independently of the other are H, $C_2$-$C_5$ alkyl, $C_1$-$C_{12}$ alkoxyalkyl, allyl, 2-hydroxyethyl or a group of formula IV in which $R^{11}$ is hydrogen, $C_1$-$C_4$ alkyl, allyl, benzyl, $C_2$-$C_5$ alkanoyl, $C_1$-$C_{12}$ alkoxy, cyclohexyloxy or $C_2$-$C_5$ alkanoyloxy, or $R^8$ and $R^9$ together are $C_4$-$C_6$ alkylene which can be interrupted by —O—, and X in the case where n=1 is as defined for $R^9$ and in the case where n=2 is a group —N($R^8$)—$R^{12}$—N($R^8$)— in which $R^{12}$ is $C_2$-$C_8$ alkylene. Especially preferred compounds of formula I are those in which n is 1 or 2, $R^1$ is a group of formula II or III, $R^2$, $R^3$, $R^4$ and $R^5$ independently of the others are H, $C_1$-$C_{12}$ alkyl, $C_1$-$C_4$ alkoxy, phenoxy, $C_2$-$C_5$ alkoxycarbonyl, $C_2$-$C_5$ alkanoyl, benzoyl, $CF_3$ or Cl, at least two of $R^2$, $R^3$, $R^4$ and $R^5$ being hydrogen, $R^6$ and $R^7$ independently of the other are phenoxy, phenyl, methoxy-substituted phenyl or a group —N($R^8$)($R^9$), $R^8$ and $R^9$ independently of the other are H, $C_1$-$C_8$ alkyl, $C_3$-$C_6$ alkoxyalkyl, allyl or a group of formula IV in which $R^{11}$ is hydrogen, methyl, benzyl, acetyl, $C_6$-$C_{12}$ alkoxy or cyclohexyloxy, or $R^8$ and $R^9$ together are $C_4$-$C_5$ alkylene which can be interrupted by —O—, and X in the case where n=1 is as defined for $R^6$ and in the case where n=2 is a group —N($R^8$)—$R^{12}$—N($R^8$)— in which $R^{12}$ is $C_4$-$C_6$ alkylene.

Preferred compounds of formula I are those in which n is 1 and $R^1$ is a group of formula II.

Especially preferred compounds are those of the formula

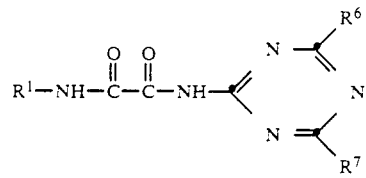

wherein $R^1$ is o-ethoxyphenyl and $R^6$ and $R^7$ are phenyl; or $R^1$ is p-phenoxyphenyl and $R^6$ and $R^7$ are phenyl; or $R^1$ is o-ethoxyphenyl, $R^6$ is morpholino and $R^7$ is dimethylamino; or $R^1$ is o-ethoxyphenyl and $R^6$ and $R^7$ are a radical of the formula

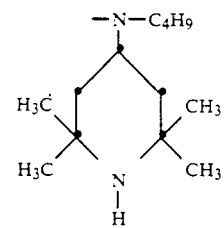

and the compound of the formula

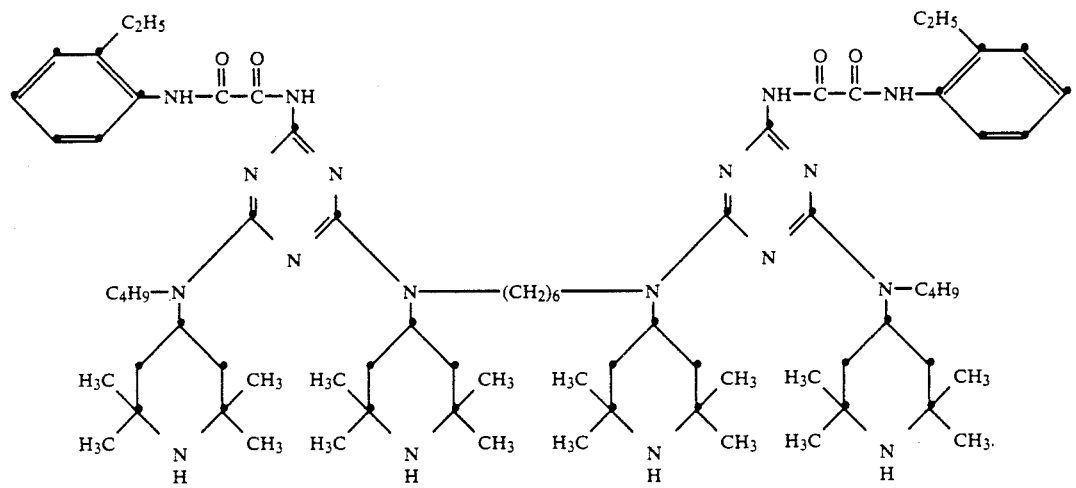
Examples of further compounds of formula I are those of the formula
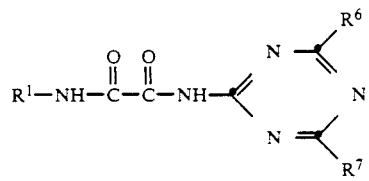
with the following substituents:
| R¹ | R⁶ | R⁷ |
|---|---|---|
| 2-ethoxyphenyl | $-N(C_2H_5)_2$ | $-N(C_2H_5)_2$ |
| 2-benzoyl-4-chlorophenyl | $-N(C_8H_{17})_2$ | $-N(C_8H_{17})_2$ |
| 2-(trifluoromethyl)phenyl | $-N(CH_3)_2$ | $-N(CH_3)_2$ |
| 4-phenoxyphenyl | $-N(C_6H_{13})_2$ | $-N(C_6H_{13})_2$ |
| 2,4-dimethylphenyl | piperidin-1-yl | piperidin-1-yl |
| 4-dodecylphenyl | phenyl | phenyl |

-continued

| R¹ | R⁶ | R⁷ |
|---|---|---|
| C₁₂H₂₅—⟨Ph⟩— | —⟨Ph(3-CH₃, 4-CH₃)⟩ | —⟨Ph(3-CH₃, 4-CH₃)⟩ |
| ⟨Ph-2-OCH₃⟩ | —N(morpholino) | —N(CH₃)₂ |
| ⟨Ph-2-C₂H₅⟩ | —N(C₄H₉)-2,2,6,6-tetramethylpiperidin-4-yl (with NH) | —N(C₂H₅)₂ |
| ⟨Ph-2-OC₂H₅⟩ | —⟨Ph-4-OH⟩ | —⟨Ph-4-OH⟩ |
| C₁₂H₂₅—⟨Ph⟩— | —⟨Ph(3-OH, 4-OC₈H₁₇)⟩ | —⟨Ph(3-OH, 4-OC₈H₁₇)⟩ |
| ⟨Ph-2-OC₂H₅⟩ | —⟨Ph-3-OH⟩ | —NH—⟨Ph⟩ |
| (CH₃)₂CH—⟨Ph⟩— | —⟨pyridyl⟩ | —⟨pyridyl⟩ |
| ⟨Ph-2-CF₃⟩ | —⟨Ph-4-SCH₃⟩ | —⟨Ph-4-SCH₃⟩ |
| ⟨Ph⟩ | —⟨Ph-4-N(CH₃)₂⟩ | —⟨Ph-4-N(CH₃)₂⟩ |
| C₉H₁₉—⟨Ph⟩— | —N(morpholino) | —N(morpholino) |

-continued

| $R^1$ | $R^6$ | $R^7$ |
|---|---|---|
| CH₃–⟨phenyl⟩ | piperidinyl with –N–C₄H₉, H₃C, CH₃, H₃C, CH₃, N–COCH₃ | piperidinyl with –N–C₄H₉, H₃C, CH₃, H₃C, CH₃, N–COCH₃ |
| C₈H₁₇OOC–⟨phenyl⟩ | –O–C(CH₃)₃ | –O–C(CH₃)₃ |
| C₄H₉OOC–⟨phenyl⟩ | ⟨phenyl⟩–OC(CH₃)₃, HO– | ⟨phenyl⟩–OC(CH₃)₃, HO– |
| C₂H₅O–⟨phenyl⟩ | –N(C₈H₁₇)₂ | –NHCOCONH–⟨phenyl⟩–OC₂H₅ |
| C₁₂H₂₅–⟨phenyl⟩ | –OC₈H₁₇ | –NHCOCONH–⟨phenyl⟩–C₁₂H₂₅ |
| ⟨phenyl with OC₄H₉⟩ | ⟨phenyl⟩ | –NHCOCONH–⟨phenyl with C₄H₉O⟩ |
| C₈H₁₇OOC–⟨phenyl⟩ | ⟨phenyl⟩–OC₄H₉, HO– | ⟨phenyl⟩–OC₄H₉, HO– |
| (CH₃)₂N–⟨triazine⟩–N(CH₃)₂ | ⟨phenyl⟩ | ⟨phenyl⟩ |
| C₈H₁₇O–⟨triazine⟩–OC₈H₁₇ | –N⟨morpholine ring⟩ | –N⟨morpholine ring⟩ |

Further examples of compounds of formula I are those of the formula

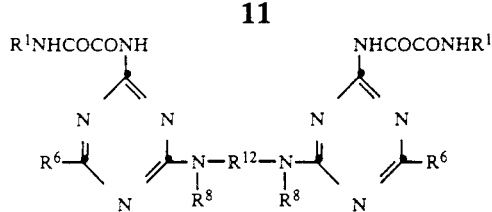

with the following substituents:

| $R^1$ | $R^6$ | $R^8$ | $R^{12}$ |
|---|---|---|---|
| ![phenyl-OC2H5] | $(C_2H_5)_2N-$ | 2,2,6,6-tetramethyl-1-methyl-piperidinyl | $-(CH_2)_6-$ |
| $C_{12}H_{25}-$phenyl | morpholino $O\diagup\diagdown N-$ | 2,2,6,6-tetramethyl-1-octyloxy-piperidinyl | $-(CH_2)_6-$ |
| $C_2H_5OOC-$phenyl | $t\text{-}C_8H_{17}$ | H | $-(CH_2)_4-$ |
| $Cl-$phenyl | $CH_3O-$phenyl | H | $-(CH_2)_3O(CH_2)_3-$ |

The oxalamides of formula I can be prepared by reacting oxalic acid ester-amides of formula V with aminotriazines of formula VI.

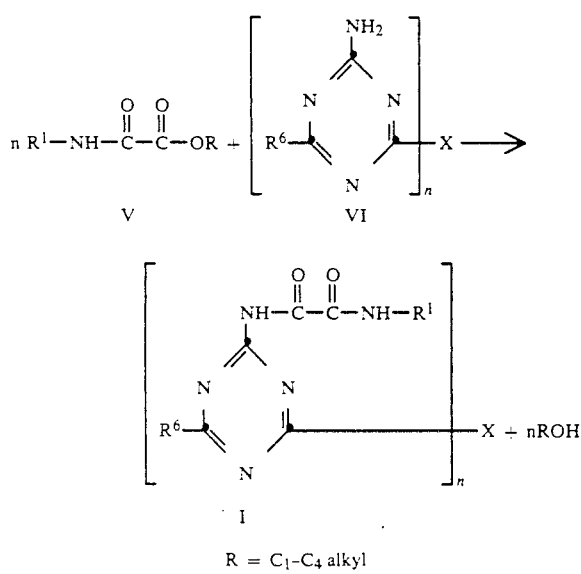

$R = C_1\text{-}C_4$ alkyl

The oxalic acid ester-amides V are known compounds or can be prepared by reacting an oxalic acid dialkyl ester or an oxalic acid monoester chloride with one mol equivalent of an amine $R^1-NH_2$.

The aminotriazines VI are also known compounds or can be preapred from the appropriate chlorotriazine by reaction with ammonia.

The reaction of V with VI can be carried out in the presence or absence of a solvent. Examples of suitable solvents are toluene, xylene or chlorobenzene. The reaction is preferably carried out without a solvent. The reaction can be accelerated by adding a basic catalyst, suitable catalysts for this purpose being, in particular, alkali metal alkoxides, hydrides or amides. The reaction can be monitored by measuring the alcohol ROH formed. Distillation of the alcohol ROH from the reaction vessel can be accelerated by flushing with an inert gas or by adding limited amounts of solvent.

Most of the compounds of formula I are solid substances which can be purified by crystallization or chromatography.

The compounds of formula I are Uv absorbers and as such are suitable as stabilizers for organic materials to protect them from damage by light.

The invention therefore further relates to the use of at least one compound of formula I according to claim 1 as a light stabilizer for organic materials and to an organic material containing at least one compound of formula I as a light stabilizer.

The materials to be stabilized can be e.g. oils, fats, waxes, photographic materials or cosmetics, but the compounds are especially suitable as stabilizers for organic polymers.

Examples of organic polymers which can be stabilized with the compounds of formula I are the following classes of polymers:

1. Polymers of monoolefins and diolefins, for example polypropylene, polyisobutylene, polybut-1-ene, polymethylpent-1-ene, polyisoprene or polybutadiene, as well as polymers of cycloolefins, e.g. of cyclopentene or norbornene, and polyethylene (which can be uncrosslinked or cross-linked), e.g. high density polyethylene (HDPE), low density polyethylene (LDPE) and linear low density polyethylene (LLDPE).

2. Mixtures of the polymers mentioned under 1), e.g. mixtures of polypropylene with polyisobutylene and of polypropylene with polyethylene (e.g. PP/HDPE, PP/LDPE) and mixtures of different types of polyethylene (e.g. LDPE/HDPE).

3. Copolymers of monoolefins and diolefins with each other or with other vinyl monomers, e.g. ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetqte copolymers or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned under 1), e.g. polypropyleneethylene/propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers.

3a. Hydrocarbon resins (e.g. $Chd_5$–$C_9$), including hydrogenated modifications thereof (e.g. tackifiers).

4. Polystyrene, poly(p-methylstyrene) and poly($\alpha$-methylstyrene).

5. Copolymers of styrene or o-methylstyrene with dienes or acrylic derivatives, e.g. styrene/butadiene, styrene/acrylonitrile, styrene/alkyl methacrylate, styrene/butadiene/alkyl acrylate, styrene/maleic anhydride and styrene/acrylonitrile/methyl acrylate; high-impact mixtures of styrene copolymers and another polymer, e.g. a polyacrylate, a diene polymer or an ethylene/propylene/diene terpolymer; and block copolymers of styrene, e.g. styrene/butadiene/styrene, styrene/isoprene/styrene, styrene/ethylene-butylene/styrene or styrene/ethylene-propylene/styrene 6. Graft copolymers of styrene or o-methylstyrene, e.g. styrene on polybutadiene; styrene on polybutadiene/styrene or polybutadiene/acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or alkyl methacrylates on polybutadiene; styrene and acrylonitrile on ethylene/propylene/diene terpolymers; styrene and acrylonitrile on polyalkyl acrylates or polyalkyl methacrylates; and styrene and acrylonitrile on acrylate/butadiene copolymers, as well as mixtures thereof with the copolymers mentioned under 5), e.g. the mixtures known as ABS, MBS, ASA or AES polymers.

7. Halogenated polymers such as polychloroprene, chlorinated rubber, chlorinated or sulfochlorinated polyethylene, and epichlorohydrin homopolymers and copolymers, and especially polymers of halogenated vinyl compounds, e.g. polyvinyl chloride, polyvinylidene chloride, polyvinyl fluoride and polyvinylidene fluoride; as well as copolymers thereof, such as vinyl chloride/vinylidene chloride, vinyl chloride/vinyl acetate or vinylidene chloride/vinyl acetate.

8. Polymers derived from $\alpha,\beta$-unsaturated acids and derivatives thereof, such as polyacrylates and polymethacrylates, polyacrylamides and polyacrylonitriles.

9. Copolymers of the monomers mentioned under 8) with each other or with other unsaturated monomers, e.g. acrylonitrile/butadiene copolymers, acrylonitrile/alkyl acrylate copolymers, acrylonitrile/alkoxyalkyl acrylate copolymers or acrylonitrile/vinyl halide copolymers, or acrylonitrile/alkyl methacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine; as well as copolymers thereof with olefins mentioned in section 1.

11. Homopolymers and copolymers of cyclic ethers, such as polyalkylene glycols, polyethylene oxide, polypropylene oxide or copolymers thereof with bisglycidyl ethers.

12. Polyacetals such as polyoxymethylene, and polyoxymethylenes containing comonomers, e.g. ethylene oxide; and polyacetals modified with thermoplastic polyurethanes, acrylates or MBS.

13. Polyphenylene oxides and sulfides and mixtures thereof with styrene polymers or polyamides.

14. Polyurethanes derived from polyethers, polyesters and polybutadienes with terminal hydroxyl groups on the one hand and from aliphatic or aromatic polyisocyanates on the other, as well as precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, and aromatic polyamides obtained from m-xylene, diamine and adipic acid; polyamides prepared from hexamethylenediamine and isophthalic and/or terephthalic acid and, if desired, an elastomer as modifier, e.g. poly-2,4,4-trimethylhexamethylene terephthalamide or poly-m-phenylene isophthalamide; block copolymers of the aforementioned polyamides with polyolefins, olefin copolymers, ionomers or chemically bonded or grafted elastomers, or with polyethers, e.g. with polyethylene glycol, polypropylene glycol or polytetramethylene glycol; and also polyamides or copolyamides modified with EPDM or ABS, and polyamides condensed during processing (RIM polyamide systems).

16. Polyureas, polyimides, polyamide-imides and polybenzimidazoles.

17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates, as well as block polyether-esters derived from hydroxyl-terminated polyethers; and also polyesters modified with polycarbonates or MBS.

18. Polycarbonates and polyester-carbonates.

19. Polysulfones, polyether-sulfones and polyetherketones.

20. Crosslinked polymers derived from aldehydes on the one hand and phenols, urea or melamine on the other, such as phenol/formaldehyde resins, urea/formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols, and vinyl compounds as crosslinking agents, and also halogenated modifications thereof of low flammability.

23. Crosslinkable acrylic resins derived from substituted acrylic acid esters, e.g. from epoxy acrylates, urethane acrylates or polyester acrylates.

24. Alkyd resins, polyester resins and acrylate resins crosslinked with melamine resins, urea resins, polyisocyanates or epoxy resins.

25. Crosslinked epoxy resins derived from polyepoxides, e.g. from bisglycidyl ethers or from cycloaliphatic diepoxides.

26. Natural polymers such as cellulose, natural rubber and gelatin, and derivatives thereof chemically modified in a polymer-homologous manner, such as cellulose acetates, cellulose propionates and cellulose butyrates, or the cellulose ethers, such as methyl cellulose; and rosins and derivatives.

27. Mixtures (polyblends) of the aforementioned polymers, e.g. PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 66 and copolymers, PA/HDPE, PA/PP and PA/PPO.

It is especially preferred to use the compounds of the invention in all kinds of lacquers. These can be pigmented or unpigmented lacquers or metallic lacquers. They can contain an organic solvent or be solvent-free, or they can be water-based lacquers.

The lacquers can contain at least one of the polymers listed above as a binder. The following are examples of lacquers with special binders:

1. Lacquers based on cold-crosslinking or hot-crosslinking alkyd, acrylate, polyester, epoxy or melamine resins or mixtures of such resins, if appropriate with the addition of an acid curing catalyst.

2. Two-component polyurethane lacquers based on acrylate, polyester or polyether resins containing hydroxyl groups and on aliphatic or aromatic polyisocyanates.

3. One-component polyurethane lacquers based on blocked polyisocyanates which are unblocked during stoving.

4. Two-component lacquers based on (poly)ketimines and aliphatic or aromatic polyisocyanates.

5. Two-component lacquers based on (poly)ketimines and an unsaturated acrylate resin, a polyacetoacetate resin or a methacrylamidoglycolate methyl ester.

6. Two-component lacquers based on polyacrylates containing carboxyl or amino groups and on polyepoxides.

7. Two-component lacquers based on acrylate resins containing anhydride groups and on a polyhydroxyl or polyamino component.

8. Two-component lacquers based on (poly)oxazolidines and acrylate resins containing anhydride groups, unsaturated acrylate resins or aliphatic or aromatic polyisocyanates.

9. Two-component lacquers based on unsaturated polyacrylates and polymalonates.

10. Thermoplastic polyacrylate lacquers based on thermoplastic acrylate resins or externally crosslinking acrylate resins in combination with etherified melamine resins.

11. Lacquer systems based on siloxane-modified acrylate resins.

12. Lacquer systems based on fluorine-modified acrylate resins.

The lacquers can also be radiation-curable lacquers. In this case, the binder consists of monomeric or oligomeric compounds which contain ethylenic double bonds and are converted to a crosslinked high-molecular form by irradiation with actinic light or with electron beams. Said binder is generally a mixture of such compounds.

The lacquers can be applied as one-coat or two-coat lacquers, the stabilizers of the invention preferably being added to the unpigmented top coat.

The lacquers can be applied to the substrates (metal, plastic, wood etc.) by the conventional processes, for example by coating, spraying, pouring, dipping or electrophoresis.

Photographic materials which can be stabilized with the compounds of formula I are, in particular, photographic colour films and colour papers. For this purpose, the stabilizers are preferably added together with the colour couplers to the appropriate colour-sensitive layers, i.e. the yellow layer, magenta layer and/or cyan layer. The stabilizers protect both the colour coupler and the developed dye from damage by light, in particular UV light.

The compounds of formula I are preferably added to the organic materials in a concentration of 0.01 to 5 % by weight, based on the material to be stabilized. It is also possible to add mixtures of two or more compounds of formula I.

The compounds of formula I can be used together with other stabilizers, for example with the following classes of stabilizers.

1. Antioxidants 1.1. Alkylated monophenols, e.g. 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones. e.g. 2,6-di-tert-butyl-4-methoxyphenol, 2,5-di-tert-butylhydroquinone, 2,5-di-tert-amylhydroquinone, 2,6-di-phenyl-4-octadecyloxyphenol.

1.3. Hydroxylated thiodiphenyl ethers, e.g. 2,2'-thiobis(6-tert-butyl-4-methylphenol), 2,2'-thiobis(4-octylphenol), 4,4'-thiobis(6-tert-butyl-3methylphenol), 4,4'-thiobis(6-tert-butyl-2-methylphenol).

1.4. Alkylidenebisphenols, e.g. 2,2'-methylenebis(6-tert-butyl-4-methylphenol), 2,2'-methylenebis(6-tert-butyl-4-ethylphenol), 2,2'-methylene-bis-[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis-[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis-(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate.

1.5. Benzyl compounds, e.g. 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis-(4-tert-butyl-3-hydroxy-2,6-dimethylbenzyl) dithiolterephthalate, 1,3,5tris-(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4hydroxybenzyl) isocyanurate.

1.6 Acylaminoohenols. e.g. 4-hydroxylauranilide, 4-hydroxystearanilide, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of β(3,5-di-tert-butyl-4-hydroxyphenyl)-propionic acid with monohydric or polyhydric alcohols, e.g. with methanol, octadecanol, hexane-1,6-diol, neopentyl glycol, thiodiethylene glycol, diethylene glycol, triethylene glycol, pentaerythritol, tris(hydroxyethyl) isocyanurate, N,N'-bis(hydroxyethyl)oxalodiamide.

1.8. Esters of β-(5-tert-butyl-4-hydroxy-3-methylphenyl)propionic acid with monohydric or polyhydric alcohols, e.g. with methanol, octadecanol, hexane-1,6-diol, neopentyl glycol, thiodiethylene glycol, diethylene glycol, triethylene glycol, pentaerythritol, tris(hydroxyethyl) isocyanurate, N,N'-bis(hydroxyethyl)oxalodiamide.

1.9. Esters of β-(3,5-dicyclohexyl-4-hydroxyphenyl)prqpionic acid with monohydric or polyhydric alcohols, e.g. with methanol, octadecanol, hexane-1,6-diol, neopentyl glycol, thiodiethylene glycol, diethylene glycol, triethylene glycol, pentaerythritol, tris(hydroxyethyl) isocyanurate, N,N'-bis(hydroxyethyl)oxalodiamide.

1.10. Amides of β-(3,5-di-tert-butyl-4-hydroxyphenyl)propionic acid, e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilizers 2.1. 2-(2'-Hydroxyphenyl)benzotriazoles. e.g. the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tertbutyl, 4'-octyloxy, 3',5'-di-tert-amyl and 3',5'-bis(α,α-dimethylbenzyl) derivatives.

2.2. 2-Hydroxybenzophenones, e.g. the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivates.

2.3. Esters of substituted or unsubstituted benzoic acids, e.g. 4-tertbutylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate.

2.4. Acrylates, e.g. ethyl or isooctyl α-cyano-β, β-diphenylacrylate, methyl α-carbomethoxycinnamate, methyl or butyl α-cyano-β-methyl-p-methoxycinnamate, methyl α-carbomethoxy-p-methoxycinnamate, N-(β-carbomethoxy-β-cyanovinyl)-2-methylindoline.

2.5. Nickel compounds, e.g. nickel complexes of 2,2'-thiobis[4-(1,1,3,3tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines. e.g. bis(2,2,6,6-tetramethylpiperidyl) sebacate, bis(1,2,2,6,6-pentamethylpiperidyl) sebacate, bis(1,2,2,6,6pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethylpiperid-4-yl)hexamethylenediamine and 4-tert-octylamino-2,6-dichloro-1,3,5-s-triazine, tris(2,2,6,6-tetramethylpiperid-4-yl) nitrilotriacetate, tetrakis(2,2,6,6-tetramethylpiperid-4-yl) butane-1,2,3,4-tetracarboxylate, 1,1'-(ethane-1,2-diyl)bis(3,3,5,5-tetramethylpiperazinone).

2.7. Oxalic acid diamides, e.g. 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert butyl-2 -ethyloxanilide and its mixture with 2-ethoxy-2'-ethyl-5,4'-di-tert-butyloxanilide, mixtures of o- and p-methoxy-disubstituted oxanilides and of o- and p-ethoxy-disubstituted oxanilides.

2.8. 2-(2-Hydroxyphenyl)-1,3,5-triazines, e.g. 2,4,6-tris(2-hydroxy-4-octyloxyphenyl)-1,3,5-triazine octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis-(2,4-dimethylphenyl)-1,3,5-triazine, 2,4-bis(2-hydroxy-4-propoxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal passivators, e.g. N,N'-diphenyloxalodiamide, N-salicylal—N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phosphonites, e.g. triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl)-4,4'- biphenylene diphosphonite, 3,9-bis(2,4-di-tert-butylphenoxy)-2,4,8,10-tetraoxa-3,9-diphosphaspiro[5,5]undecane.

5. Peroxide scavengers. e.g. esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers. e.g. copper salts in combination with iodides and/or phosphorus compounds, and salts of divalent manganese.

7. Basic co-stabilizers, e.g. melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example calcium stearate, zinc stearate, magnesium stearate, sodium ricinoleate, potassium palmitate, antimony pyrocatecholate or tin pyrocatecholate.

8. Nucleating agents, e.g. 4-tert-butylbenzoic acid, adipic acid, diphenylacetic acid.

The plastics or lacquers which are stabilized with compounds of formula I can contain further additives such as those conventionally used in the art, e.g. antistatic agents, plasticizers, lubricants, flame retardants, blowing agents, solvents, fillers, reinforcing agents, pigments, curing accelerators, photoinitiators, flow control agents or adhesion promoters.

The following Examples describe the preparation and use of compounds of formula I. Parts and percentages are by weight, unless indicated otherwise.

EXAMPLE 1

N'-[4,6-Bis(diethylamino)-1,3,5-triazin-2-yl]—N'-(2-ethoxyphenyl)oxalamide

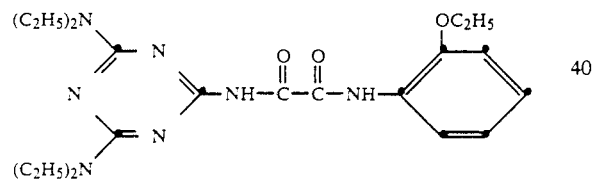

A mixture of 11.9 g of 2-amino-4,6-bis(diethylamino)-1,3,5-triazine (50 mmol) and 11.2 g of methyl N-(2-ethoxyphenyl)oxalamate (50 mmol) is melted under nitrogen at 100° C. and 0.72 g (10 mmol) of KOCH: is then added. The melt is heated to 150°-160° C., with stirring, 10 ml of xylene are added dropwise at this temperature and the methanol formed is distilled off. After 5 h, the reaction mixture is cooled, taken up in 70 ml of toluene and washed with three times 50 ml of water. The toluene solution is dried over $Na_2SO_4$ and evaporated under vacuum. An oil remains which solidifies on standing. Recrystallization from 50 ml of ligroin gives 12.1 g of white crystals melting at 97°-100° (compound n° 1).

EXAMPLE 2

N'-[4,6-Bis(di-2-ethylhexylamino)-1,3,5-triazin-2-yl]—N'-(2-benzoyl-4-chlorphenyl)oxalamide

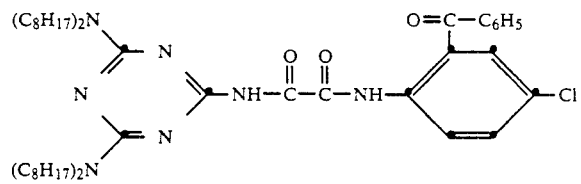

A mixture of 28.7 (50 mmol) of 2-amino-4,6-bis(di-2-ethyhexylamino)-1,3,5-triazine and 17.5 g (55 mmol) of methyl N-(2-benzoyl-4-chlorphenyl)oxalamate is melted under nitrogen at 110° C. and 0.11 g (5 mmol) of $LiNH_2$ is added. The melt is heated to 160° C., with stirring. 40 ml of xylene are added dropwise at this temperature and the methanol formed is distilled off. After 8 h, the reaction mixture is cooled and taken up in toluene. The toluene solution is washed with water, dried over $Na_2SO_4$ and evaporated. The oily residue is chromatographed over silica gel (petroleum ether:ethyl acetate 97:3). A yellow resin melting at about 43° C. is obtained as the main fraction (compound n° 2).

Analysis $C_{50}H_{78}ClN_7O_3$ Calc. 70.54 % C 10.39 % H 12.80 % N.

Found 70.6% C 10.37 % H 12.16% N.

EXAMPLES 3-13

The compounds of the formula

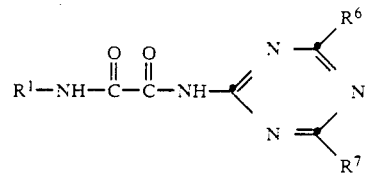

listed in Table 1 are prepared analogously to Example 1 or 2.

TABLE 1

| Compound No. | $R^1$ | $R^6=R^7$ | catalyst | m.p.(°C.) |
|---|---|---|---|---|
| 3 | ![Cl, CO—C6H5 phenyl] | —N(C2H5)2 | LiNH2 | 193-6 |
| 4 | ![CF3 phenyl] | —N(C2H5)2 | LiNH2 | 100-3 |

TABLE 1-continued

| Compound No. | R¹ | R⁶=R⁷ | catalyst | m.p.(°C.) |
|---|---|---|---|---|
| 5 | C₆H₅O—C₆H₄— | —N(C₂H₅)₂ | LiNH₂ | 92-5 |
| 6 | 2-OC₂H₅—C₆H₄— | —N(CH₂CH(C₂H₅)—C₄H₉)₂ | LiNH₂ | oil |
| 7 | triazine with R⁶, R⁷ | —N(CH₂CH(C₂H₅)—C₄H₉)₂ | t-C₄H₉OK | oil |
| 8 | 3,5-(CH₃)₂—C₆H₃— | piperidino | LiNH₂ | 209-20 |
| 9 | 2-OC₂H₅—C₆H₄— | piperidino | LiNH₂ | 238-40 |
| 10 | 3-Cl-4-(CO—C₆H₅)—C₆H₃— | piperidino | LiNH₂ | 257-8 |
| 11 | C₆H₅—O—C₆H₄—C₆H₄— | | LiNH₂ | 227-32 |
| 12 | 4-C₁₂H₂₅—C₆H₄— | 3,4,5-(OCH₃)₃—C₆H₂— | LiNH₂ | 138-42 |
| 13 | 2-OC₂H₅—C₆H₄— | —N(CH₂—CH=CH₂)₂ | t-C₄H₉OK | 93-6 |

EXAMPLE 14

Compound of the Formula

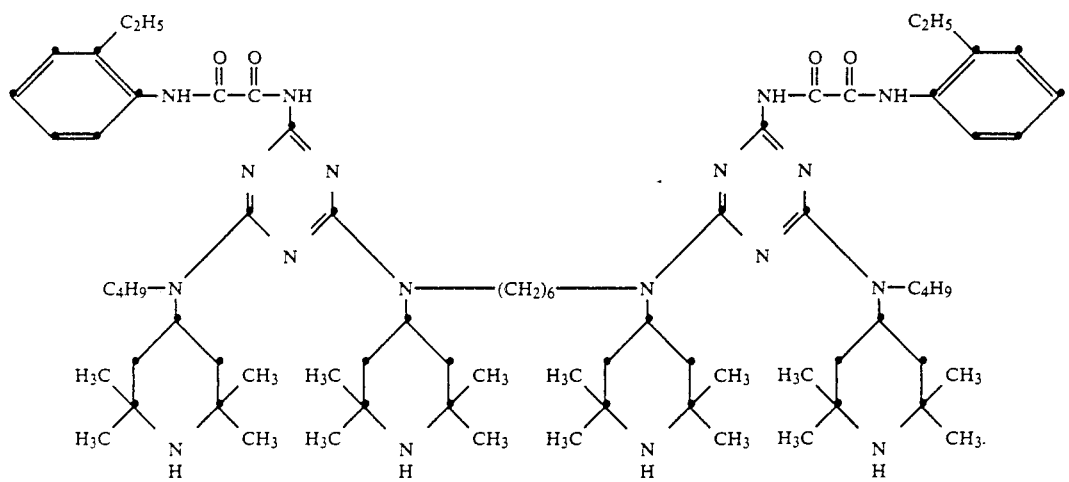

This compound is prepared analogously to Example 1 from the appropriate bis(aminotriazine) and 2 mol equivalents of methyl N-(2-ethylphenyl)oxalamate in the presence of NaOCH$_3$ as the catalyst. The product melts at 223–5° C. (compound n° 14).

EXAMPLES 15–21

The compounds of the formula

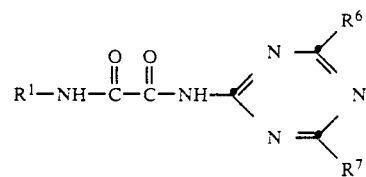

listed in Table 2 are prepared analogously to Example 1.

TABLE 2

| Comp. No. | R$^1$ | R$^6$ | R$^7$ | catalyst | m.p.(°C.) |
|---|---|---|---|---|---|
| 15 | 2-OC$_2$H$_5$-phenyl | C$_4$H$_9$—N— (2,2,6,6-tetramethylpiperidin-4-yl) | = R$^6$ | NaOCH$_3$ | 147–9 |
| 16 | 2-OC$_2$H$_5$-phenyl | —N(morpholino) | —N(CH$_3$)$_2$ | NaOCH$_3$ | 215–7 |
| 17 | 2-OC$_2$H$_5$-phenyl | —N(morpholino) | = R$^6$ | NaOCH$_3$ | 228–30 |
| 18 | 4-C$_{12}$H$_{25}$-phenyl | —N(morpholino) | = R$^6$ | NaOCH$_3$ | 96–8 |
| 19 | 2-C$_2$H$_5$-phenyl | —N(morpholino) | = R$^6$ | NaOCH$_3$ | 207–10 |

TABLE 2-continued

| Comp. No. | R¹ | R⁶ | R⁷ | catalyst | m.p.(°C.) |
|---|---|---|---|---|---|
| 20 | C₁₂H₂₅-[phenyl] | —N(CH₃)₂ | = R⁶ | NaOCH₃ | 92–5 |
| 21 | [phenyl with OC₂H₅] | —N(CH₃)₂ | = R⁶ | NaOCH₃ | 161–4 |

EXAMPLE 22

Stabilization of a two-coat metallic lacquer

A varnish is prepared from the following components:

58.3 parts of an acrylic resin (Viacryl® VC 373, Vianova, Vienna)

27.3 parts of a melamine resin (Maprenal® MF 590, Hoechst AG)

4.0 parts of an aromatic solvent mixture (Solvesso® 150, Esso AG)

1.0 parts of a flow control agent (Baysilon®, Bayer AG)

5.4 parts of xylene 4.0 parts of butyl glycol acetate 2% based on the solids content, of the stabilizers listed in Table 3, dissolved in 5–10 ml of xylene, is added. The varnish is diluted with a mixture of butyl acetate, butyl glycol acetate and xylene (1:1:1) until it is sprayable, and sprayed on to aluminium sheets primed with an aluminium-pigmented surfacer based on polyester resin/melamine resin. The samples are stoved for 30 minutes at 130° C. The resulting varnish has a dry layer thickness of 40–45 μm.

The samples are weathered in an UVCON® rapid weatherometer from Atlas, with a cycle of 8 h of UV irradiation at 70° C. and 4 h of condensation at ° C. The weathering time taken for cracking to start is measured.

TABLE 3

| Stabilizer | Weathering Time to Cracking |
|---|---|
| none | 800 h |
| 2% compound Nr. 1 | 1200 h |
| 2% compound Nr. 6 | 1200 h |
| 2% compound Nr. 18 | 1600 h |
| 2% compound Nr. 20 | 1200 h |
| 2% compound Nr. 21 | 1600 h |

EXAMPLE 23

Stabilization of a two-coat lacquer

The varnish described in Example 22 is applied to aluminium sheets primed with a grey-pigmented two-component epoxy resin lacquer, and stoved for minutes at 130° C.

The samples are weathered outdoors for 6 months in Florida (5° south). The DOI (distinctness of reflected image) is measured according to method ASTM E 430-78. The results are listed in Table 4. The DOI value is a criterion for the surface gloss of the sample.

TABLE 4

| Stabilizer | DOI (as % of initial value) after 6 months in Florida |
|---|---|
| none | 15% |
| 2% compound No. 1 | 87% |
| 2% compound No. 21 | 58% |

What is claimed is:

1. A compound of formula I

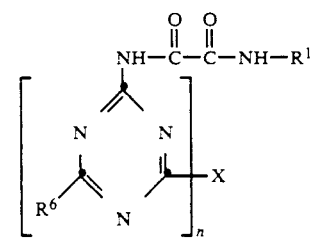

wherein n is an integer from 1 to 4, $R^1$ is a group of formula II or III

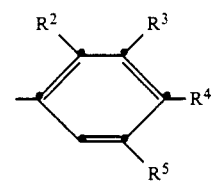

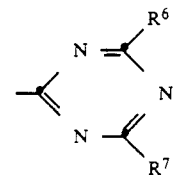

$R^2$, $R^3$, $R^4$, and $R^5$ independently of the others are hydrogen, $C_1$–$C_{18}$ alkyl, $C_5$–$C_{12}$ cycloalkyl, $C_7$–$C_9$ phenylalkyl, hydroxyl, $C_1$–$C_{12}$ alkoxy, phenoxy, phenoxy substituted by $C_1$–$C_4$ alkyl, $C_1$–$C_4$ alkoxy, halogen or hydroxyl, $C_2$–$C_{18}$ alkoxycarbonyl, $C_2$–$C_{18}$ alkylaminocarbonyl, a group —CO—O—$R^{10}$, $C_3$–$C_5$ alkenyl, $C_3$–$C_5$ alkynyl, $C_2$–$C_{12}$ alkanoyl, benzoyl, $C_1$–$C_8$ perfluoroalkyl chlorine, fluorine or bromine, with the proviso that the group of formula II contains no more than three hydroxyl groups, $R^6$ and $R^7$ independently of the other are $C_1$–$C_{12}$ alkoxy, $C_3$–$C_{12}$ cycloalkoxy, phenoxy, phenoxy substituted by $C_1$–$C_{12}$ alkyl, $C_3$–$C_5$ alkenyloxy, phenyl, pyridyl, phenyl substituted by hydroxyl, $C_1$–$C_{12}$ alkyl, $C_1$–$C_{12}$ alkoxy, $C_1$–$C_{12}$ alkylthio or $C_1$–$C_{12}$ mono-alkylamino or dialkylamino, or a group —N(R⁸)(R⁹), wherein $R^8$ and $R^9$ independently of the other are hydrogen, $C_1$-$C_{18}$ alkyl, $C_3$-$C_{18}$ alkyl interrupted by one or more —O—, $C_3$-$C_5$ alkenyl, $C_2$-$C_4$ hydroxyalkyl or a group of formula IV

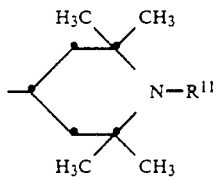

wherein $R^{11}$ is hydrogen, $C_1$-$C_4$ alkyl, $C_3$-$C_5$ alkenyl, $C_7$-$C_9$ phenylalkyl, $C_2$-$C_{12}$ alkanoyl, hydroxyl, $C_1$-$C_{12}$ alkoxy, $C_5$-$C_{12}$ cycloalkoxy or $C_2$-$C_{18}$ alkanoyloxy, or $R^8$ and $R^9$ together are $C_4$-$C_9$ alkylene which can be interrupted by —O—, and in the case where $R^8$ is hydrogen, $R^9$ can also be a group

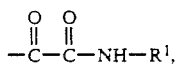

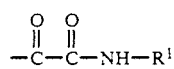

$R^{10}$ is a group of formula IV and X in the case where n=1 is as defined for $R^6$, in the case where n=2 is a group —N(R⁸)—R¹²—N(R⁸)—,

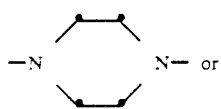

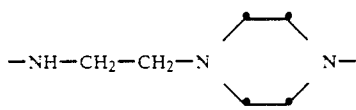

wherein $R^{12}$ is $C_2$-$C_{12}$ alkylene or $C_4$-$C_{12}$ alkylene interrupted by one or more —O—, in the case where n=3 is a group

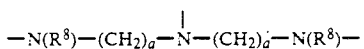

in the case where n=4 is a group

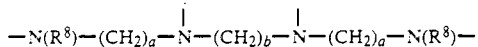

wherein a and b are 2 or 3.

2. A compound according to claim 1 of formula I in which n is 1 or 2, $R^1$ is a group of formula II or III, $R^2$, $R^3$, $R^4$ and $R^5$ independently of the others are H, $C_1$-$C_{12}$ alkyl, cyclohexyl, benzyl, hydroxyl, $C_1$-$C_{12}$ alkoxy, phenoxy, phenoxy substituted by $C_1$-$C_4$ alkyl, $C_1$-$C_4$ alkoxy or Cl, $C_2$-$C_5$ alkoxycarbonyl, allyl, propargyl, $C_2$-$C_5$ alkanoyl, benzoyl, $CF_3$, Cl, F or Br, at least one of $R^2$, $R^3$, $R^4$ and $R^5$ being hydrogen, $R^6$ and $R^7$ independently of the other are $C_1$-$C_{12}$ alkoxy, cyclohexyloxy, phenoxy, tolyloxy, allyloxy, phenyl, phenyl substituted by $C_1$-$C_4$ alkoxy or $C_1$-$C_4$ alkylthio, or a group —N(R⁸)(R⁹), $R^8$ and $R^9$ independently of the other are H, $C_2$-$C_{12}$ alkyl, $C_3$-$C_{12}$ alkoxyalkyl, allyl, 2-hydroxyethyl or a group of formula IV in which $R^{11}$ is hydrogen, $C_1$-$C_4$ alkyl, allyl, benzyl, $C_2$-$C_5$ alkanoyl, $C_1$-$C_{12}$ alkoxy, cyclohexyloxy or $C_2$-$C_5$ alkanoyloxy, or $R^8$ and $R^9$ together are $C_4$-$C_6$ alkylene which can be interrupted by —O—, and X in the case where n=1 is as defined for $R^6$ and in the case where n=2 is a group —N(R⁸)—R¹²—N(R⁸)— in which $R^{12}$ is $C_2$-$C_8$ alkylene.

3. A compound according to claim 1 of formula I in which n is 1 or 2, $R^1$ is a group of formula II or III, $R^2$, $R^3$, $R^4$ and $R^5$ independently of the others are H, $C_1$-$C_{12}$ alkyl, $C_1$-$C_4$ alkoxy, phenoxy, $C_2$-$C_5$ alkoxycarbonyl, $C_2$-$C_5$ alkanoyl, benzoyl, $CF_3$ or Cl, at least two of $R^2$, $R^3$, $R^4$ and $R^5$ being hydrogne, $R^6$ and $r^7$ independently of the other are phenoxy, phenyl, methoxy-substituted phenyl or a group —N(R⁸)(R⁹), $R^8$ and $R^9$ independently of the other are H, $C_1$-$C_8$ alkyl, $C_3$-$C_6$ alkoxyalkyl, allyl or a group of formula IV in which $R^{11}$ is hydrogne, methyl, benzyl, acetyl, $C_6$-$C_{12}$ alkoxy or cyclohexyloxy, or $R^8$ and $R^9$ together are $C_4$-$C_5$ alkylene which can be interrupted by —O—, and X in the case where n=1 is as defined for $R^6$ and in he case where n=2 is a group —N(R⁸)—R¹²—N(R⁸)— in which $R^{12}$ is $C_4$-$C_6$ alkylene.

4. A compound according to claim 1 of formula I in which n is 1.

5. A compound according to claim 1 of formula I in which $R^1$ is a group of formula II.

6. A compoudn according to claim 1 of formula VII

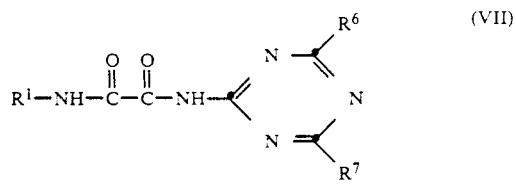

where $R^1$ is o-ethoxyphenyl and $r^6$ and $R^7$ are phenyl; or $R^1$ is p-phenoxyphenyl and $R^6$ and $R^7$ are phenyl; or $R^1$ is o-ethoxyphenyl, $R^6$ is morpholino and $R^7$ is dimethylamino; or $R^1$ is o-ethoxyphenyl and $R^6$ and $R^7$ are a radical of the formula

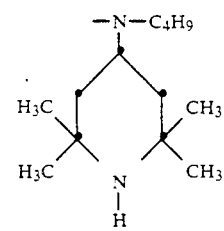

7. A compound according to claim 1 of the formula

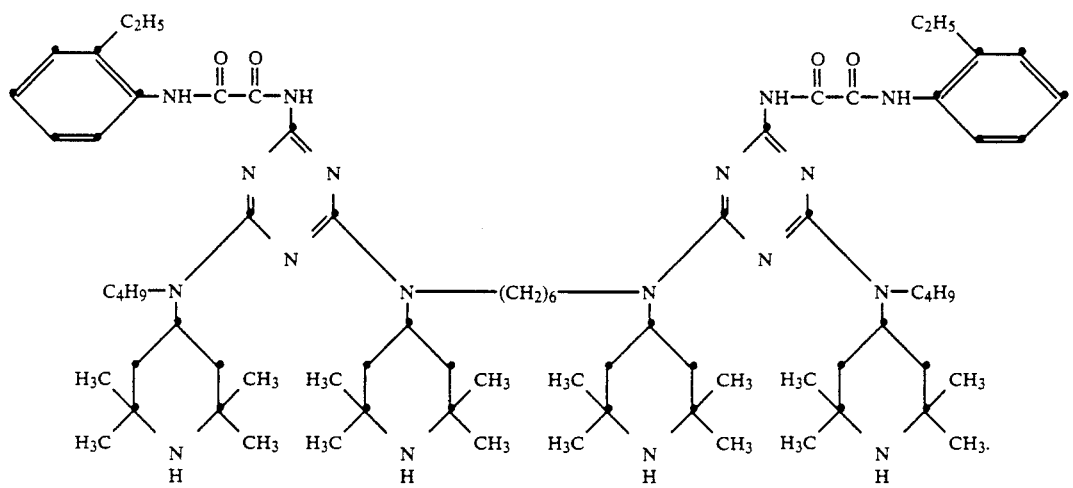

8. A composition stabilized against damage by actinic light which comprises
 (a) an organic polymer, and
 (b) an effective stabilizing amount of a compound of formula I according to claim 1.

9. A composition according to claim 8 wherein the organic polymer is a lacquer.

10. A composition according to claim 8 wherein the effective stabilizing amount of component (b) is 0.1 to 5% by weight based on component (a).